United States Patent [19]

Huskins et al.

[11] 4,430,885
[45] Feb. 14, 1984

[54] APPARATUS FOR DETERMINING THE BURN RATE OF UNCURED PROPELLANT

[75] Inventors: Chester W. Huskins; Leroy J. Williams, both of Huntsville, Ala.

[73] Assignee: The United States of America as represented by the Secretary of the Army, Washington, D.C.

[21] Appl. No.: 383,402

[22] Filed: Jun. 1, 1982

[51] Int. Cl.³ .............................................. G01N 33/22
[52] U.S. Cl. ......................................................... 73/35
[58] Field of Search ...................................... 73/35, 167

[56] References Cited

U.S. PATENT DOCUMENTS

| | | | |
|---|---|---|---|
| 2,681,563 | 6/1954 | Golden | 73/35 |
| 2,924,964 | 2/1960 | Minke | 73/35 |
| 3,191,426 | 6/1965 | Wilhite et al. | 73/35 |
| 3,580,049 | 5/1971 | Cardwell et al. | 73/35 |

Primary Examiner—Gerald Goldberg
Assistant Examiner—John E. Chapman, Jr.
Attorney, Agent, or Firm—Robert P. Gibson; Anthony T. Lane; Harold W. Hilton

[57] ABSTRACT

A closed vessel apparatus for rapidly determining the burning rate of uncured propellant. Apparatus includes a closed vessel enclosing a propellant in a holder. An ignition wire is mounted in the vessel for igniting the propellant. A pressure transducer is provided for detecting the pressure rise in the vessel and an electronic circuit triggers the start and stop of pressure integration. This data is fed to a data print out circuit.

4 Claims, 4 Drawing Figures

APPARATUS FOR DETERMINING THE BURN RATE OF UNCURED PROPELLANT

DEDICATORY CLAUSE

The invention described herein may be manufactured, used, and licensed by or for the Government for governmental purposes without the payment to use of any royalties thereon.

BACKGROUND OF THE INVENTION

The ballistic properties of the propellant used in shoulder-fired in-tube burning weapons, must be very reliable for the protection of the gunner.

Propellants burning either faster or slower than that specified for the missile can be hazardous. Slow burning propellants can result in after launch tube burning or in the case of very fast burning, rupture of the missile or launch tube. Therefore, quality assurance procedures and tests to assure the missile components reliability and performance are especially important in this type of missile system.

It is, therefore, an object of the present invention to provide apparatus to determine rapidly the burning rate of uncured propellant so that adjustments may be made in the propellant composition before the propellant is loaded into a missile motor.

SUMMARY OF THE INVENTION

Apparatus for determining the burn rate of uncured propellant, including a closed vessel enclosing a sample holder which has been filled under vacuum with an uncured propellant. An ignition wire is positioned in contact with the propellant for igniting the propellant. A pressure transducer is provided in the vessel to detect the pressure rise. An electronic circuit is provided to trigger the start of pressure integration in a burn rate analyzer at a preset voltage level and to stop the integration at a preset voltage. A data print out circuit gives a print out of the area integrated between the two pressure points.

DESCRIPTION OF THE PREFERRED EMBODIMENT

The burning rate of a propellant generally increases rather rapidly as the pressure in the system increases. When a propellant is burned in a closed vessel without venting the combustion gases as they are generated, the pressure in the vessel begins to rise as soon as the propellant burning is initiated and as the pressure rises in the closed system, the burning rate increases further with increasing pressure rise rate and burning rate. If the mass and shape of the propellant sample is the same, then the pressure rise in a closed vessel would be expected to be more rapid for a faster burning propellant than for the slower burning composition.

Figure 1:
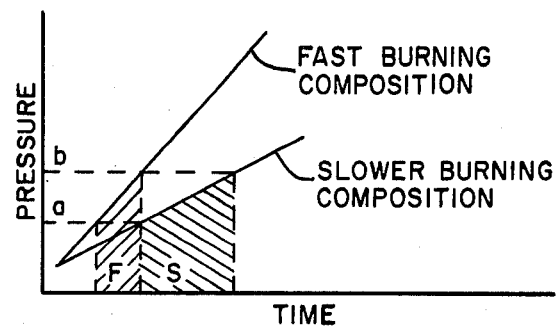
FIG. 1 is a graph of burning characteristics of propellants in a closed vessel.

Therefore, the slope of the pressure rise for faster burning propellant will be higher than for the slower burning composition. If two pressure levels $P_a$ and $P_b$ are selected and the area under the curve between the two pressure rise points is obtained, this data can be used to compare the relative burning rates of several compositions. This is shown graphically in FIG. 1. For the fast burning composition Number 1 the area (F) under the curve is less than that for composition Number 2 (area S) which is a slower burning composition than Number 1 composition. The pressure trigger levels $P_a$ and $P_b$ were the same for each composition to initiate and stop the area integration for each curve. The sample weight and configuration are important and must be adjusted to the vessel volume. These parameters determine the slope of the pressure rise and the range of pressure integration that can be used. The slope of the pressure rise is also very dependent upon the propellant burning rate. For a slow burning rate composition, it may be necessary to select relatively large sample 8–9 grams, a large diameter sized holder, and a small volume closed vessel to achieve a rapid pressure rise that would give a reasonable area from the pressure integration. On the other hand, a fast burning propellant may require a relatively large volume vessel and small diameter sample container to achieve the desired pressure rise rate and pressure integration. Since the sample size, vessel volume, range of pressure integration and propellant burning rate are very important and contribute to the rate of pressure rise in the vessel and the area under the curve, it is necessary to select these conditions for the propellant composition under test.

Figure 2:
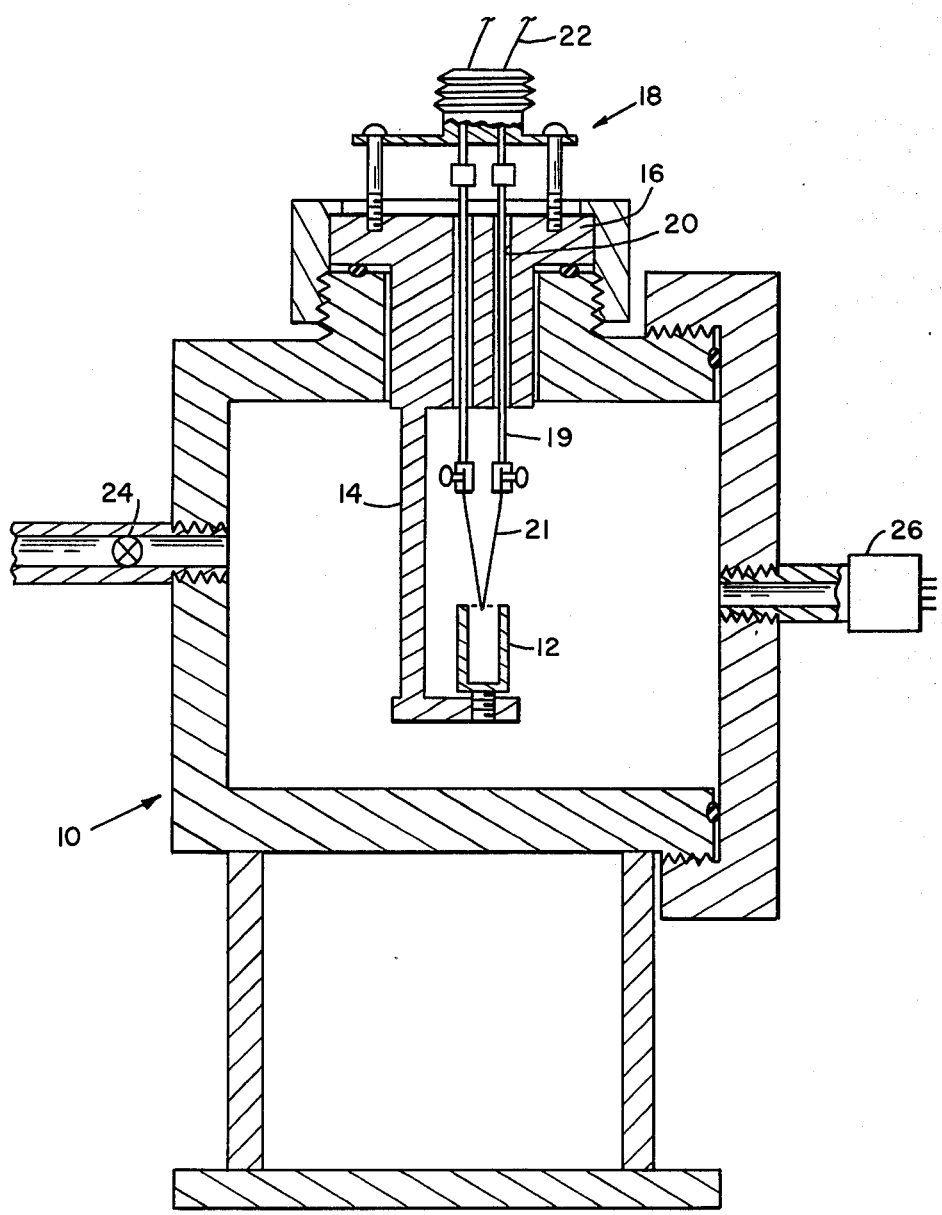
FIG. 2 is a cross-sectional view of the closed vessel enclosing a propellant sample.

As seen in FIG. 2 a closed vessel 10 is provided for enclosing a holder 12 having uncured propellant therein. The vessel includes a support 14 for support of holder 12. An upper closure member 16 closes off the vessel and supports an ignition wire assembly 18. The ignition wire assembly includes a pair of members 19 which extend through openings 20 to electrical connections 22 which are connected to an electrical source (not shown). An ignition wire 21 is provided in the lower portions of members 19. A sealant (not shown) is provided in openings 20. A vent valve 24 and a pressure transducer 26 is supported in vessel 10 and is disposed in communication with the interior thereof.

Figure 3:
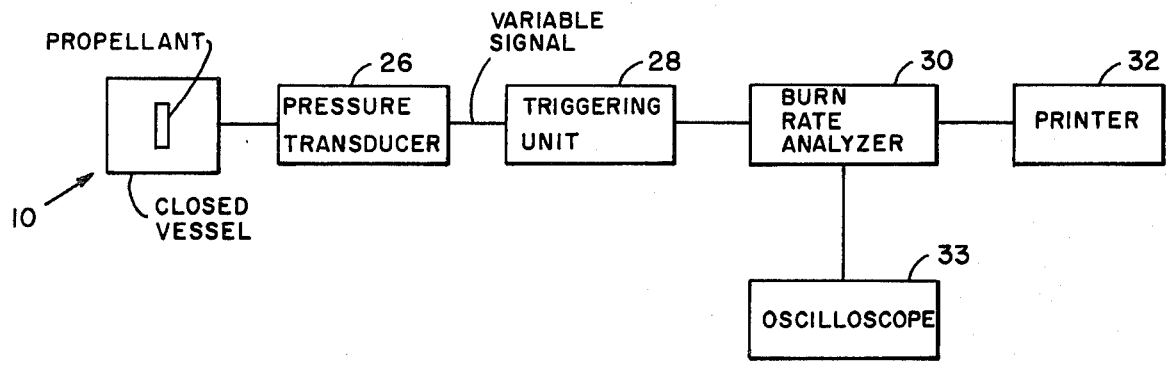
FIG. 3 is a diagrammatic view illustrating data and instrument flow for determining the burn rate of uncured propellant.

As seen in FIG. 3 a triggering unit 28 is connected to pressure transducer 26 and a burn rate analyzer 30 is connected to triggering unit 28. A printer 32 and oscilloscope 33 is connected to analyzer 30.

Burn rate analyzer 30 (FIG. 4) includes a DC current amplifier 34 connected to the pressure transducer 26 and to a voltage controlled oscillator 36 which is connected to a frequency counter 38. A timer 40 is connected to frequency counter 38. A pair of voltage comparison circuits 42 and 44 is provided as the triggering unit 28 to start and stop the frequency counter. Printer 32 is connected to frequency counter 38.

The operational procedure is as follows:

A small propellant sample is removed from the mixer at the end of mix, but prior to adding the small amount of curing agent. The selected sample holder (example 0.625 inch (15.9 mm) diameter × 1 inch (25.4 mm) deep) is then filled under vacuum with the propellant. It is then mounted on the sample holder 12 with ignition wire 18 resting on the top surface of the propellant. The sample holder with ignition wire is placed in the closed vessel and the vessel sealed. The propellant is then ignited by applying a necessary current to the ignition wire. The pressure transducer 26 in the bomb will then detect the pressure rise. As the pressure rises, triggering unit 28 triggers the start of pressure integration at a preset voltage level and will stop the pressure integration at a preset voltage. These data are then fed into analyzer 30 and printer 32 which gives a print out of the area integrated under the curve between the two pressure points. In addition, the time interval between the pressure integral points is recorded.

In one embodiment of the present invention, a 500 pounds per square inch absolute (psia) (3.45 MP$_a$(Mega Pascal) pressure transducer with an output voltage of 20 millivolts at rated pressure is used. The variable signal from the pressure transducer is fed into the analyzer unit 30 through triggering unit 28 which provides the start and stop trigger gates to the analyzer unit. The triggering unit provides adjustable pressure controls so that the start and stop trigger points are selected and the pressure differentials between start and stop triggering can be varied. For visual reference, the pressure curve is displayed on a storage oscilloscope along with the integration window showing the start and stop points.

Figure 4:
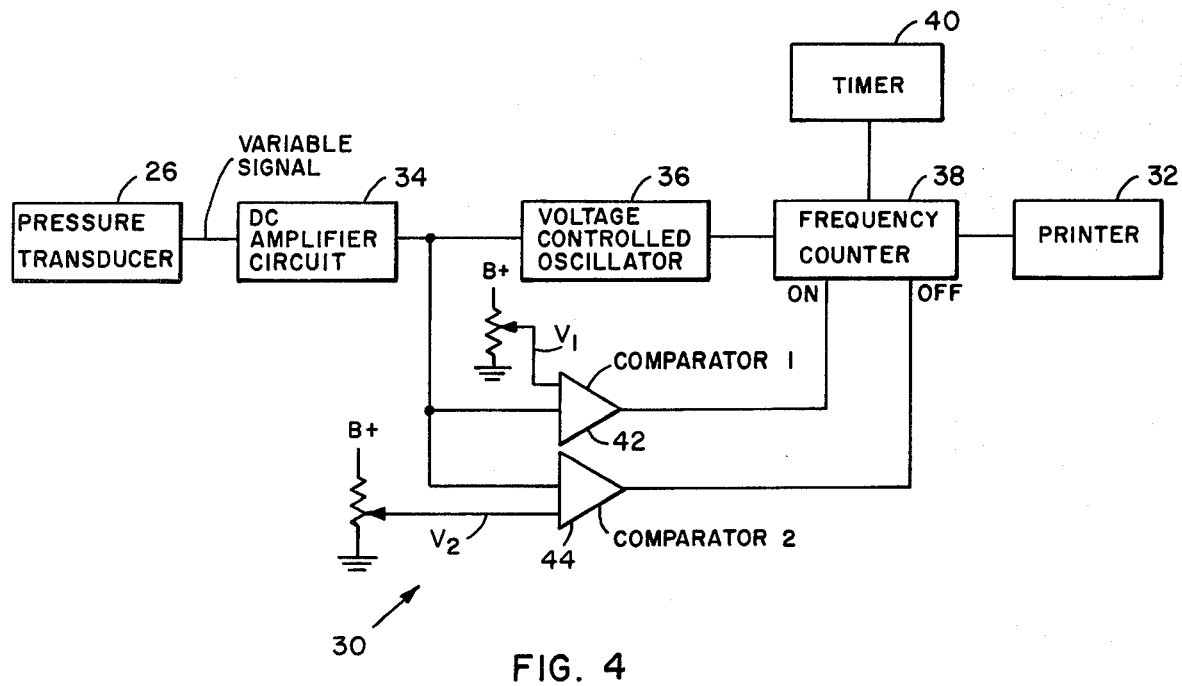
FIG. 4 is a block diagram of the burn rate analyzer used in conjunction with the closed vessel of FIG. 2.

The first member of analyzer 30 is the DC amplifier 34 (FIG. 4). The pressure curve rise time is in hundreds of milliseconds. The amplified pressure curve must now be integrated. The most simple technique is to convert the voltage to a directly proportional frequency (5 volts=5000 Hz, 6 volts=6000 Hz, etc.)

The pressure signal is fed to voltage controlled oscillator 36 which accomplishes the conversion. Linearity of the voltage to frequency converter is essential to the accuracy of the integration. The frequency counter 38 reads the signal from the oscillator. The frequency counter is started and stopped by two voltage comparison circuits 42 and 44. A reference voltage is fed to one side of each comparator while the amplified signal from circuit 34 is fed to the other side. When the voltage from the amplifier is equal to the voltage applied through the potentiometer the output of the comparator goes from zero volts to a five volt level. When the first comparator goes high, the frequency counter is started. Timer circuit 40 is also simultaneously started. When the second comparator goes high, the timer and frequency counters are stopped. The number shown by the frequency counter is directly proportional to the integrated pressure.

Another method of measuring a pressure curve would be to have a digital minicomputer take the data at a high rate from the DC amplifier and do the integration using a numerical method.

Burn rate analyzer 30 is an Anadex Burning Rate Analyzer model Number CD 11575Q produced by Anadex Instrument Company, 7833 Haskel Avenue, Van Nuys, Calif., 91406. Analyzer 30 consists of the main unit and the printer. This unit along with the printer performs the following calculations:

Gate time—Total time elapsed during gate displayed in microseconds.

Integral of temperature—Total of temperature units accumulated during gate time.

Integral of pressure—Total pressure units accumulated during gate time.

Rate=c/gate time—c represents an external constant to provide a unit per second reading.

Average temperature—Integral of temperature/gate time. Provides average value of temperature during gate time.

Average pressure—Integral of pressure/gate time. Provides average value of pressure during gate time.

Triggering unit 28 is manufactured by the Systems Service Corporation, Huntsville, AL, and is identified as Model ATU-101. The triggering unit provides start and stop triggers to the burn analyzer.

We claim:
1. A closed vessel apparatus for rapidly determining the burning rate of a sample of uncured propellant comprising:
   a. a closed vessel having said uncured propellant therein;
   b. ignition means in contact with said propellant sample for ignition thereof;
   c. a pressure transducer mounted in said vessel for detecting the pressure rise therein responsive to pressure after ignition of said propellant;
   d. analyzer means connected to said pressure transducer and disposed for integrating the area under a pressure versus time curve between predetermined pressure points;
   e. triggering means for the start of said analyzer at a preset voltage level and the stop of said analyzer at a second preset voltage level, said preset voltage levels corresponding to said predetermined pressure points; and,
   f. print out means for providing a print out of the area integrated under the curve between the two pressure points, whereby the area is taken as a measure of the burning rate of the uncured propellant.

2. Apparatus as in claim 1 wherein said vessel includes an upper closure member having a support extending therefrom for support of said sample holder inside said vessel.

3. Apparatus as in claim 2 wherein said ignition means comprises an ignition wire assembly carried by said upper closure member, said assembly having an ignition wire for engagement with said propellant sample.

4. Apparatus as in claim 3 including a vent valve mounted on said vessel and in communication with the interior of said closed vessel.

* * * * *